United States Patent [19]
Honda et al.

[11] Patent Number: 5,579,104
[45] Date of Patent: Nov. 26, 1996

[54] APPARATUS APPLIED TO SPECTROSCOPY

[75] Inventors: Akira Honda; Seiji Kojima, both of Otsu, Japan

[73] Assignee: Shimadzu Corporation, Kyoto, Japan

[21] Appl. No.: 430,217

[22] Filed: Apr. 27, 1995

[30] Foreign Application Priority Data

Apr. 28, 1994 [JP] Japan ..................... 6-114322

[51] Int. Cl.⁶ ......................................... B01N 21/00
[52] U.S. Cl. ..................... 356/73; 356/312; 356/316; 356/326
[58] Field of Search ........................ 356/312, 315, 356/319, 311, 73, 316, 323–328, 329–334

[56] References Cited

U.S. PATENT DOCUMENTS

| | | | |
|---|---|---|---|
| 4,406,541 | 9/1983 | Tomoff et al. | 356/312 |
| 4,981,357 | 1/1991 | Minakawa et al. | 356/333 X |
| 5,155,547 | 10/1992 | Casper et al. | 356/316 |
| 5,311,277 | 5/1994 | Sasaki et al. | 356/312 |
| 5,383,019 | 1/1995 | Farrell et al. | 356/316 |
| 5,424,832 | 6/1995 | Nakano et al. | 356/312 |

*Primary Examiner*—K. Hantis
*Attorney, Agent, or Firm*—Oliff & Berridge

[57] ABSTRACT

A spectroscopic apparatus applicable to both ICP (inductively coupled plasma) emission spectroscopy and atomic absorption spectrometry is provided. The spectroscopic apparatus includes a sample unit on which a plasma torch for ICP emission spectroscopy and a heating tube for atomic absorption spectrometry are mounted. A control unit shifts the sample unit to place a plasma flame that is on an end of the plasma torch in front of the light inlet of a spectroscopic unit when the apparatus is operating in the ICP emission spectroscopic mode and to place a central axis of the heating tube in front of the light inlet when the apparatus is operating in the atomic absorption spectrometric mode. The control unit also shifts the apparatus to a two stage spectral mode for ICP emission spectroscopy and to a one stage spectral mode for atomic absorption spectrometry.

6 Claims, 6 Drawing Sheets

APPARATUS APPLIED TO SPECTROSCOPY

The present invention relates to an apparatus applicable to both ICP (inductively coupled plasma) emission spectroscopy and atomic absorption spectrometry.

BACKGROUND OF THE INVENTION

ICP emission spectroscopy and atomic absorption spectrometry are generally used for qualitative and quantitative analyses of metal elements included in samples. ICP emission spectroscopy heats the sample to extremely high temperatures and is thus preferably applied to analyses of metals with high boiling point, such as titanium (Ti) and vanadium (V), and multi-element analyses. Atomic absorption spectrometry has lower heating temperatures than ICP emission spectroscopy and is thus preferably applied to analyses of metals with low boiling point, such as sodium (Na) and potassium (K). There are, however, many samples which can be analyzed both by ICP emission spectroscopy and atomic absorption spectrometry. In some cases, an appropriate one of the analyses is selected by considering the concentration of a target element in a liquid sample or the sensitivity of a spectroscopic apparatus applied. In other cases, both ICP emission spectroscopy and atomic absorption spectrometry are used to analyze a sample.

Conventionally, independent and separate apparatuses are used for ICP emission spectroscopy and atomic absorption spectrometry. Both apparatuses are necessary when a wide variety of samples are supposed to be analyzed. For routine analyses of various samples, the operator is required to move between the two apparatuses and repeat the troublesome and time-consuming operations on the apparatuses.

SUMMARY OF THE INVENTION

The object of the present invention is thus to provide an apparatus applicable to both ICP (inductively coupled plasma) emission spectroscopy and atomic absorption spectrometry.

In order to realize the above and other related objects, the present invention is directed to a spectroscopic apparatus including:

(a) ICP emission unit for exciting a sample to a plasma to produce a light including an emission spectrum of said sample;

(b) atomic absorption unit for heating and atomizing a sample in a graphite tube and allowing a light from a light source to pass through said atomized sample;

(c) first spectroscopic unit for separating a light passed through a first light inlet to produce a first spectrum with a first spectral element;

(d) second spectroscopic unit for separating a light passed through a second light inlet to produce a second spectrum with a second spectral element;

(e) light detection unit for measuring an intensity of a light; and (f) control unit operable in an ICP emission spectroscopic mode and in an atomic absorption spectrometric mode, where the control unit leads the light from said ICP emission unit to said first light inlet, introduces the light separated by said first spectroscopic unit to said second light inlet, and introduces the light separated by said second spectroscopic unit to said light detector unit in the ICP emission spectroscopic mode, and leads the light emitted from the light source and passed through said atomic absorption unit to said first light inlet and introduces the light separated by said first spectroscopic unit to said light detector unit in the atomic absorption spectrometric mode.

According to a preferable application, the apparatus further includes a switch valve for switching a gas supply from an inert gas source between the ICP emission unit and the atomic absorption unit, where the control unit activates the switch valve to connect the gas supply from the inert gas source to the ICP emission unit in the ICP emission spectroscopic mode and to connect the gas supply from the inert gas source to the atomic absorption unit in the atomic absorption spectrometric mode.

The following are actual operations of the control unit in the ICP emission spectroscopic mode. The control unit first leads the light from the ICP emission unit to the first light inlet. In concrete operations, the control unit may shift a sample table, on which the ICP emission unit and the atomic absorption unit are mounted, relative to the first spectroscopic unit to make the light from the ICP emission unit enter the first spectroscopic unit, or alternatively introduce only the light from the ICP emission unit to the first spectroscopic unit by means of a light reflector without moving the ICP emission unit or the atomic absorption unit. The control unit then introduces the light separated by the first spectroscopic unit to the second light inlet for further separation into a spectrum with high resolving power by the second spectroscopic unit. The light from the ICP emission unit has a sufficiently high intensity to allow further separation by the second spectroscopic unit. The light separated by the second spectroscopic unit is eventually detected and analyzed by the light detector unit.

In the atomic absorption spectrometric mode, the control unit works in the following manner. The control unit leads the light emitted from the atomic absorption unit to the first light inlet. In concrete operations, the control unit may shift a sample table, on which the ICP emission unit and the atomic absorption unit are mounted, relative to the first spectroscopic unit to make the light from the atomic absorption unit enter the first spectroscopic unit, or alternatively introduce only the light from the atomic absorption unit to the first spectroscopic unit by means of a light reflector without moving the ICP emission unit or the atomic absorption unit. The light separated by the first spectroscopic unit is detected and analyzed by the light detector unit.

Flows of an inert gas are required in the ICP emission unit for a carrier gas to carry a sprayed sample to a plasma torch and a plasma gas to excite the sample to a plasma. A flow of an inert gas is also required in the atomic absorption unit for protecting a heating tube from erosion and discharging vapor impurities prior to atomization of a sample. The control unit activates the switch valve synchronously with the above operations and supplies a gas flow from an inert gas source to either the ICP emission unit or the atomic absorption unit.

These and other objects, features, aspects, and advantages of the present invention will become more apparent from the following detailed description of the preferred embodiments with the accompanying drawings.

DESCRIPTION OF PREFERRED EMBODIMENTS

Figure 1:
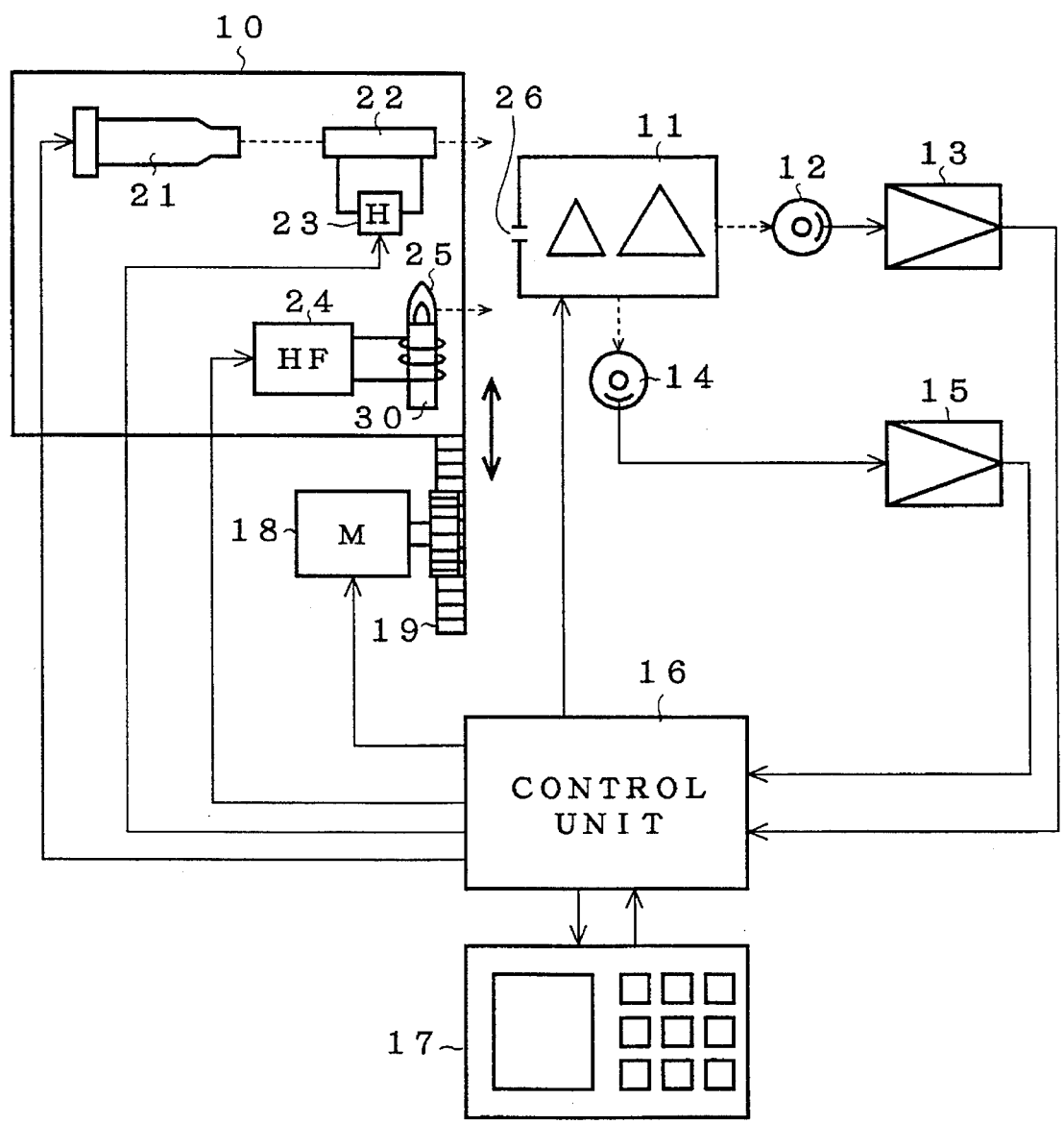
FIG. 1 is a block diagram illustrating a general structure of an apparatus applied to both ICP emission spectroscopy and atomic absorption spectrometry, as a first embodiment of the present invention.
Figure 2:
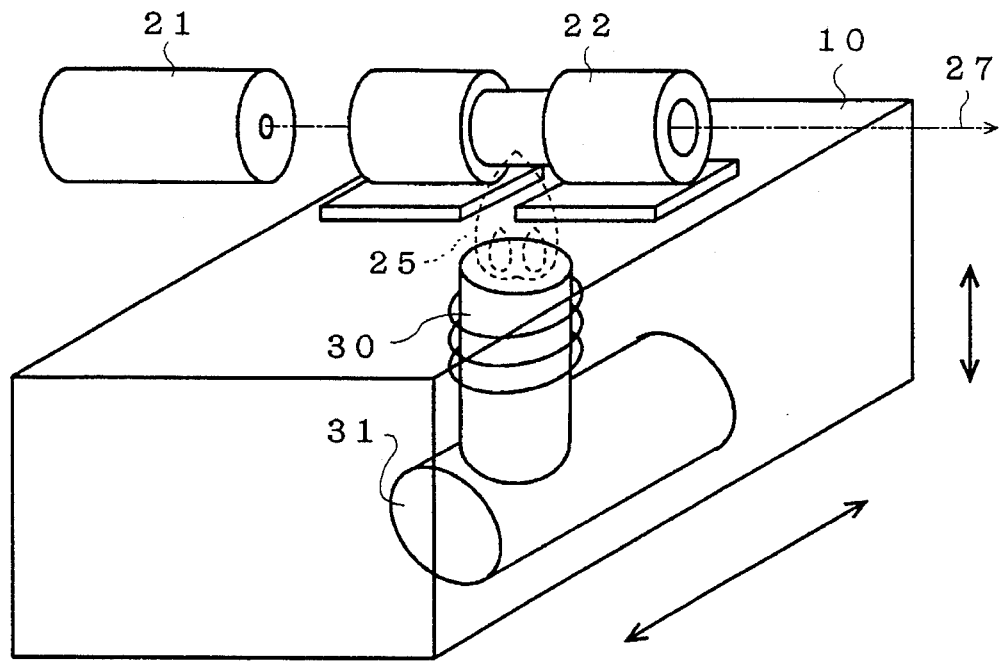
FIG. 2 is a perspective view showing an exemplified structure of the sample unit.

FIG. 1 illustrates a general structure of an apparatus applied to both ICP (inductively coupled plasma) emission spectroscopy and atomic absorption spectrometry, as a first embodiment of the present invention. The apparatus includes a sample unit 10, a spectroscopic unit 11, a first detector 12, a second detector 14, a control unit 16, and a console 17. The sample unit 10 is provided with various elements for atomic absorption spectrometry and ICP emission spectroscopy. The elements for atomic absorption spectrometry include a hollow cathode lamp 21 working as a light source, a heating tube 22 for heating and atomizing a sample, and a power source (H) 23 for supplying power to the heating tube 22, whereas those for ICP emission spectroscopy include a plasma torch 30 and a high-frequency power source (HF) 24 for generating plasma. All these elements on the sample unit 10 are movable relative to the spectroscopic unit 11 by means of a motor 18 and a driving mechanism 19. In another possible structure as shown in FIG. 2, the hollow cathode lamp 21 may be fixed in front of a light inlet 26 of the spectroscopic unit 11, while the heating tube 22 and the plasma torch 30 (and a sampling tube 31 for supplying the sprayed sample to the plasma torch 30) are on the movable portion of the sample unit 10.

Figure 3:
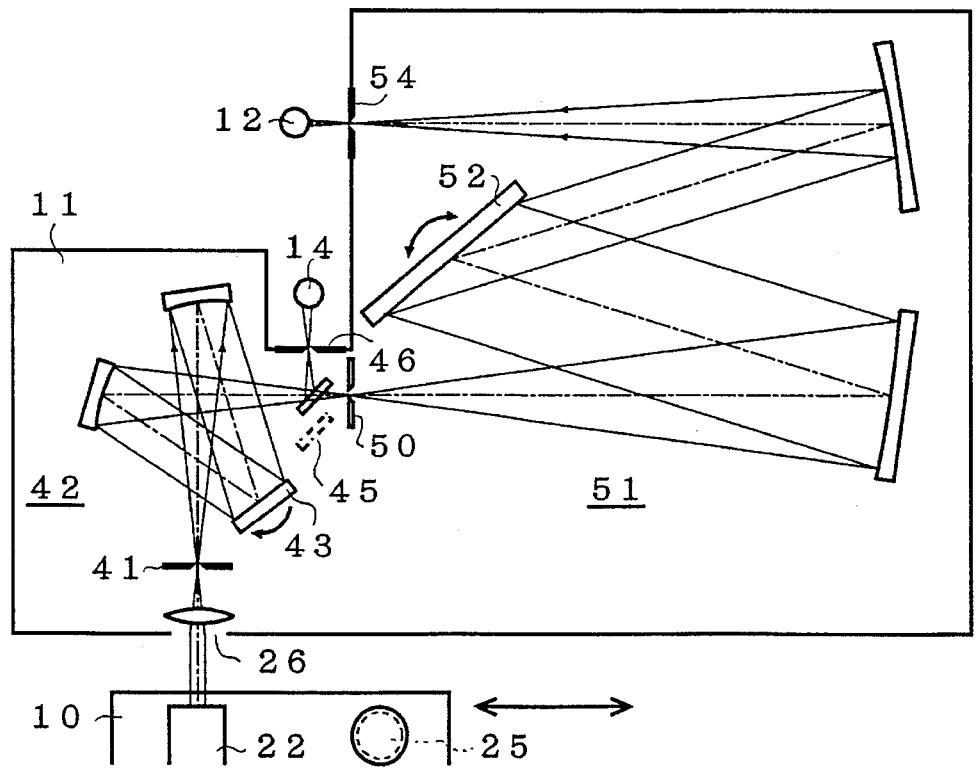
FIG. 3 is a plan view illustrating an arrangement of optical system in the spectroscopic unit.

The spectroscopic unit 11 includes a preliminary spectroscopic chamber 42 with a preliminary spectral element 43 and a primary spectroscopic chamber 51 with an echelle spectral element 52 as illustrated in FIG. 3. A movable light reflector 45 is disposed immediately before an intermediate slit 50 interposed between the preliminary spectroscopic chamber 42 and the primary spectroscopic chamber 51. The light reflector 45 placed in the optical path allows a spectrum produced in the preliminary spectroscopic chamber 42 to be detected by the second detector 14. The light reflector 45 placed out of the optical path allows the spectrum produced in the preliminary spectroscopic chamber 42 to be led into the primary spectroscopic chamber 51, where the light is further separated into a spectrum with large linear separation or high resolving power and detected by the first detector 12.

The control unit 16 transmits signals to the spectroscopic unit 11 to continuously rotate the preliminary spectral element 43 and reciprocatingly rotate the echelle spectral element 52, thereby executing the wavelength scanning of the light passed through the light inlet 26. The control unit 16 receives detection signals from the first and the second detectors 12 and 14 via respective amplifiers 13 and 15 and analyzes a sample by referring to wavelength scanning signals.

Operations of the apparatus of the first embodiment are described in detail, when the apparatus is applied to ICP emission spectroscopy or atomic absorption spectrometry. When the operator selects an atomic absorption spectrometric mode on the console 17, the control unit 16 shifts the sample unit 10 to place a central axis 27 of the heating tube 22 (see FIG. 2) on the center of the light inlet 26 of the spectroscopic unit 11. The control unit 16 also moves the light reflector 45 of the spectroscopic unit 11 into the optical path (position shown by the solid line in FIG. 3). A press of a start button on the console 17 after a dropwise supply of a sample into the heating tube 22 manually by the operator or automatically with a sampler drives the control unit 16, which transmits a control signal to the power source 23 to start heating of the heating tube 22 according to a predetermined heating program and lights up the hollow cathode lamp 21. The light emitted from the hollow cathode lamp 21 passes through the sample atomized in the heating tube 22 and enters the spectroscopic unit 11 via an inlet slit 41 of the light inlet 26. The incident light is separated to a spectrum by the preliminary spectral element 43 in the spectroscopic unit 11, reflected by the light reflector 45, and transmitted towards a second outlet slit 46. The preliminary spectral element 43 is previously set to have a predetermined angle. This allows only a resonance absorption spectrum of a target element to pass through the second outlet slit 46 and to be detected by the second detector 14. The control unit 16 quantitatively analyzes the sample based on a detection signal from the second detector 14.

When the operator selects an ICP emission spectroscopic mode on the console 17, the control unit 16 shifts the sample unit 10 to place an upper portion of the plasma torch 30 (plasma flame 25) in front of the light inlet 26 of the spectroscopic unit 11. The control unit 16 also moves the light reflector 45 of the spectroscopic unit 11 out of the optical path (position shown by the broken line in FIG. 3). After feeding a plasma gas into the plasma torch 30 through valve operations (described later), the control unit 16 transmits a control signal to the high-frequency power source 24 to produce the plasma flame 25. After the plasma flame 25 is stabilized, a sample is fed into the sampling tube 31, where the sample is highly ionized to a plasma. The light emitted from the plasma flame 25, including an emission spectrum from the sample, enters the preliminary spectroscopic chamber 42 via the inlet slit 41 of the light inlet 26 and is separated to a spectrum by the preliminary spectral element 43. As a result of separation, a spectrum of a predetermined wavelength range is led into the primary spectroscopic chamber 51 via the intermediate slit 50. The incident light is further separated to a spectrum with high resolving power by the echelle spectral element 52 in the primary spectroscopic chamber 51. This allows only a light of a predetermined wavelength to pass through a first outlet slit 54 and to be detected by the first detector 12. The control unit 16 implements the wavelength scanning by varying the angle of the preliminary spectral element 43 and that of the echelle spectral element 52, and qualitatively analyzes the sample based on a detection signal from the first detector 12.

Quantitative analysis of the sample is realized by a specific orientation of the preliminary spectral element 43 and the echelle spectral element 52, which allows only an emission spectrum of a target element to pass through the first outlet slit 54.

Figure 4:
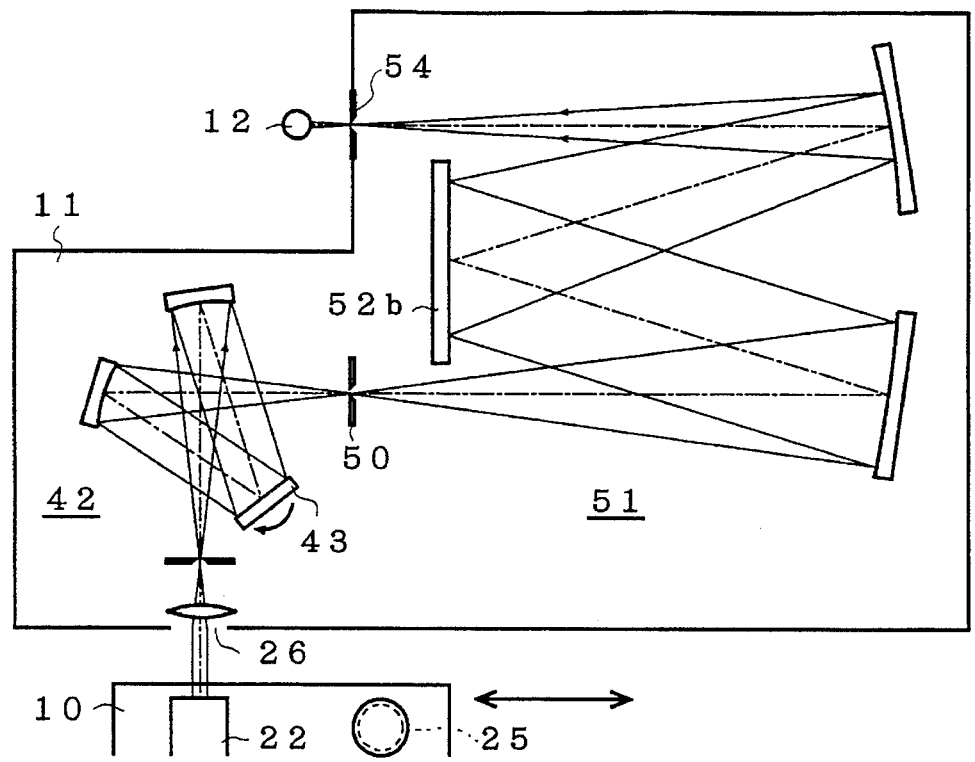
FIG. 4 is a plan view illustrating another arrangement of optical system in the spectroscopic unit.

Although separate detectors 12 and 14 are used for ICP emission spectroscopy and atomic absorption spectrometry in the present embodiment, only one detector 12 may be used commonly as shown in FIG. 4. In this modified example, the echelle spectral element 52 is replaced by a plane light reflector 52b in the ICP emission spectroscopic mode. In a preferable structure, a rear face of the echelle grating 52 forms the plane light reflector 52b, which is inverted by 180 degrees in the ICP emission spectroscopic mode. The plane light reflector 52b allows the spectrum produced by the preliminary spectral element 43 and the intermediate slit 50 to directly pass through the outlet slit 54. Such modification does not require the second detector 14, the corresponding amplifier 15, or the light reflector 45 and thereby simplifies the structure of the apparatus.

Figure 6:
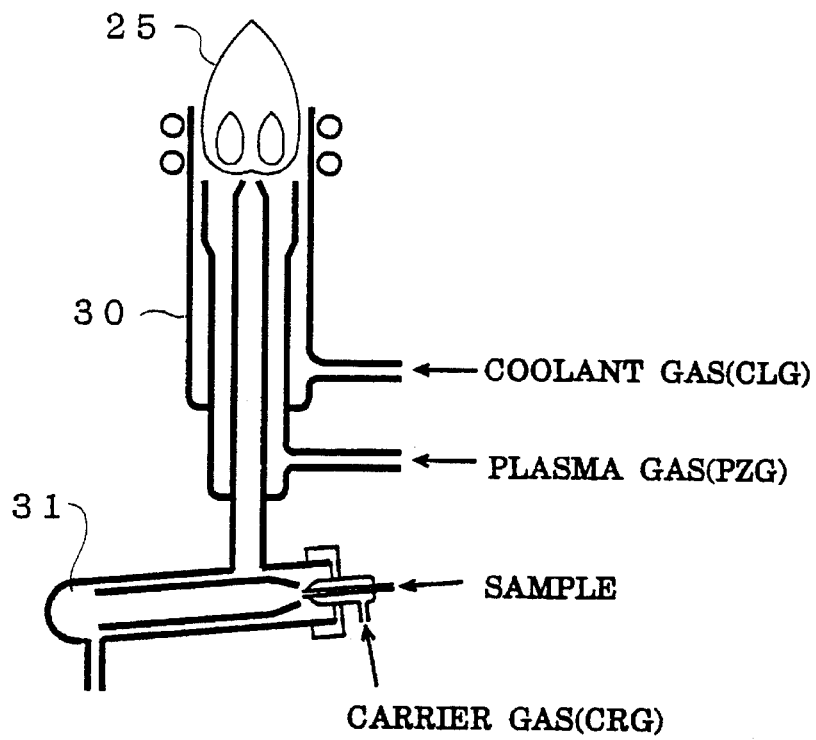
FIG. 6 is a cross sectional view illustrating a plasma torch.
Figure 7:
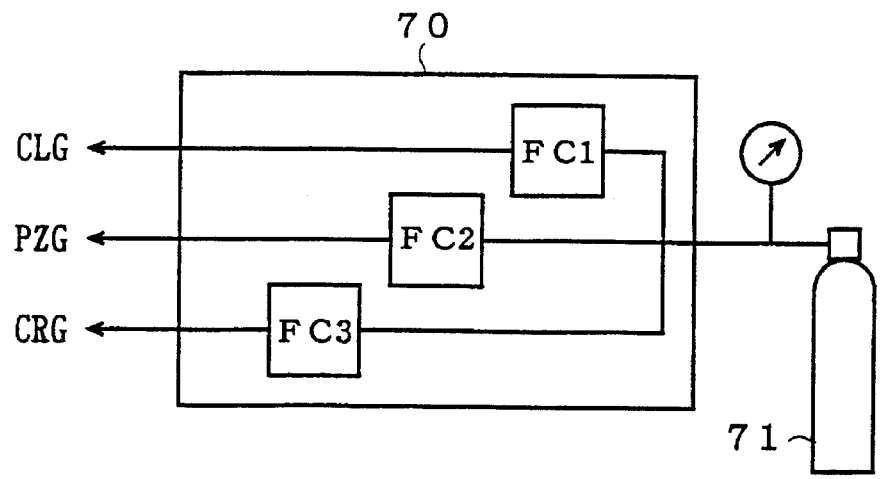
FIG. 7 is a gas distribution diagram in a conventional ICP emission spectroscope.

Referring to FIG. 6, three gas flows required for and supplied to the plasma torch 30 include a plasma gas for generating the plasma flame 25, a coolant gas for cooling and protecting the whole plasma torch 30 and its high-frequency coil, and a carrier gas for feeding the sample atomized in the sampling tube 31 to the plasma torch 30. Argon (Ar) gas is generally used for these gas flows, and the flow rate is 0.4 through 1.5 l/min for the coolant gas, 10 through 20 l/min for the plasma gas, and 0.4 through 1.5 l/min for the carrier gas. A conventional ICP emission spectroscope as illustrated in FIG. 7 is provided with a flow control unit 70 including flow control valves FC1, FC2, and FC3 for distributing a gas flow from an Ar gas tank 71 and regulating the distributions to have the respective flow rates.

Figure 8:
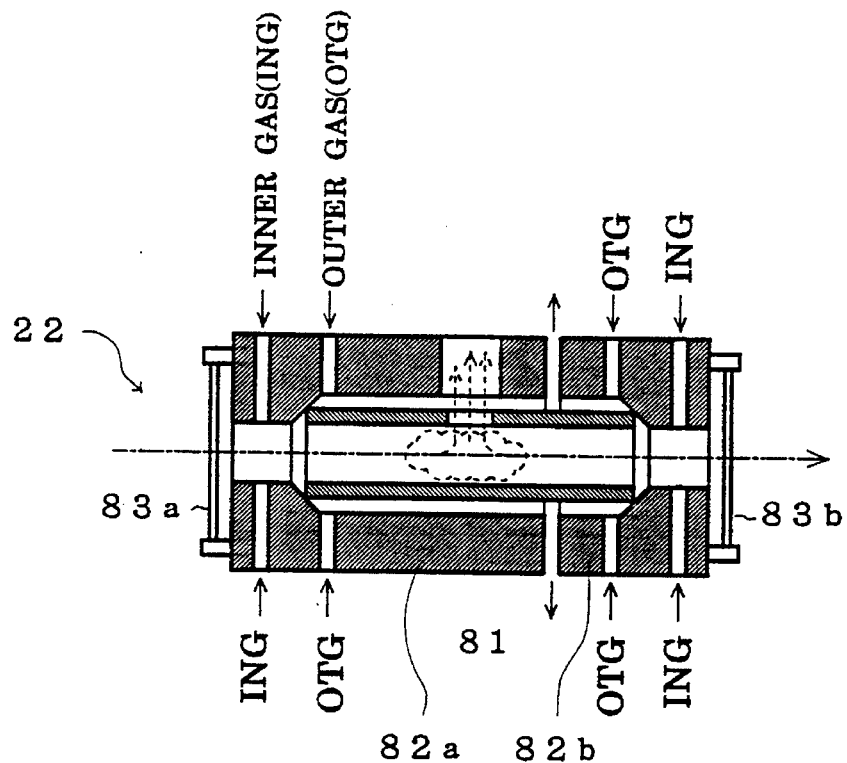
FIG. 8 is a cross sectional view showing a heating tube used for atomization of a sample.
Figure 9:
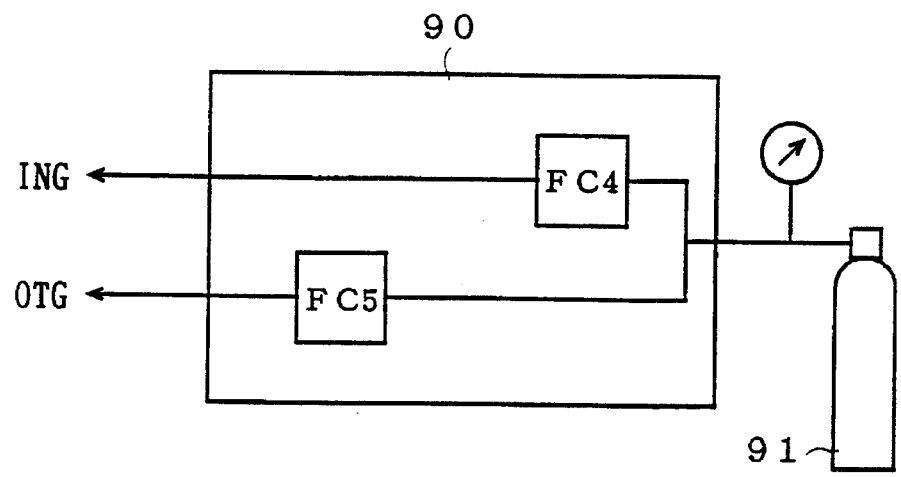
FIG. 9 is a gas distribution diagram in a conventional atomic absorption spectrometer.

As illustrated in FIG. 8, the heating tube 22 includes a graphite tube 81, two electrodes 82a and 82b for clamping the graphite tube 81, and window plates 83a and 83b arranged on respective ends of the electrodes 82a and 82b. Both the electrodes 82a and 82b clamping the graphite tube 81 function as an outer tube for covering and protecting the graphite tube 81, besides heating the graphite tube 81 with the large electric current supplied from the power source 23. The graphite tube 81 is heated to extremely high temperatures for atomization of the sample. The graphite tube 81 exposed to the air is worn out significantly at such high temperatures. A plurality of conduits for an inner gas (ING) are formed in the electrodes 82a and 82b, outside the positions in contact with the respective end faces of the graphite tube 81 but inside the window plates 83a and 83b. A plurality of conduits for an outer gas (OTG) are also arranged inside the positions in contact with the respective end faces of the graphite tube 81. An inert gas (generally Ar gas) flowing through these conduits protects the graphite tube 81 from oxidizing erosion. These conduits also work to discharge vapor impurities produced in drying and ashing processes prior to atomization of the sample from the graphite tube 81. A conventional atomic absorption spectrometer as illustrated in FIG. 9 is provided with a flow control unit 90 including flow control valves FC4 and FC5 for distributing a gas flow from an Ar gas tank 91 and regulating the distributions to have predetermined flow rates. The preferable flow rate ranges from 0.4 to 1.5 l/min for both the outer gas and the inner gas.

Figure 5:
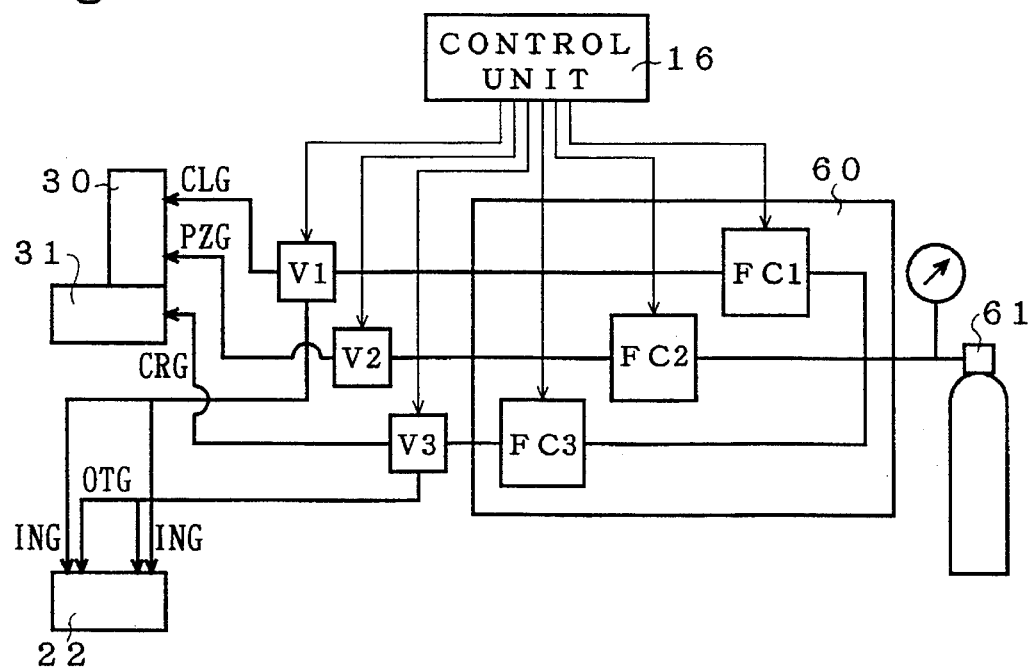
FIG. 5 is a gas distribution diagram showing distribution of an inert gas to the sample unit of the first embodiment.

As illustrated in FIG. 5, the apparatus of the embodiment applicable to both ICP emission spectroscopy and atomic absorption spectrometry includes three flow control valves FC1, FC2, and FC3, two three-way valves V1 and V3, and one open/close valve V2 for switching a flow path and controlling the flow rate. In the ICP emission spectroscopic mode, the control unit 16 transmits control signals to the two three-way valves V1 and V3 to switch the flow path towards the plasma torch 30 and the sampling tube 31 and an open signal to the open/close valve V2, simultaneously with moving the sample unit 10 and the light reflector 45. The control unit 16 also outputs control signals to the three flow control valves FC1, FC2, and FC3 to set predetermined flow rates. An Ar gas flow from a gas tank 61 is regulated to have the predetermined flow rates by the respective flow control valves FC1, FC2, and FC3 of the flow control unit 60 and fed to the plasma torch 30 and the sampling tube 31 via the valves V1, V2, and V3.

In the atomic absorption spectrometric mode, the control unit 16 transmits control signals to the two three-way valves V1 and V3 to switch the flow path towards the heating tube 22 and a close signal to the open/close valve V2, simultaneously with moving the sample unit 10 and the light reflector 45. The control unit 16 also outputs control signals to the flow control valves FC1 and FC3 to set predetermined flow rates. An Ar gas flow from the gas tank 61 is regulated to have the predetermined flow rates by the respective flow control valves FC1 and FC3 of the flow control unit 60 and fed to the outer gas conduits and the inner gas conduits of the heating tube 22 via the three-way valves V1 and V3. The apparatus of the present embodiment applied to both ICP emission spectroscopy and atomic absorption spectrometry automatically implements the selected spectroscopic analyses without any manual switching operations of the gas flow path by the operator.

Figure 10:
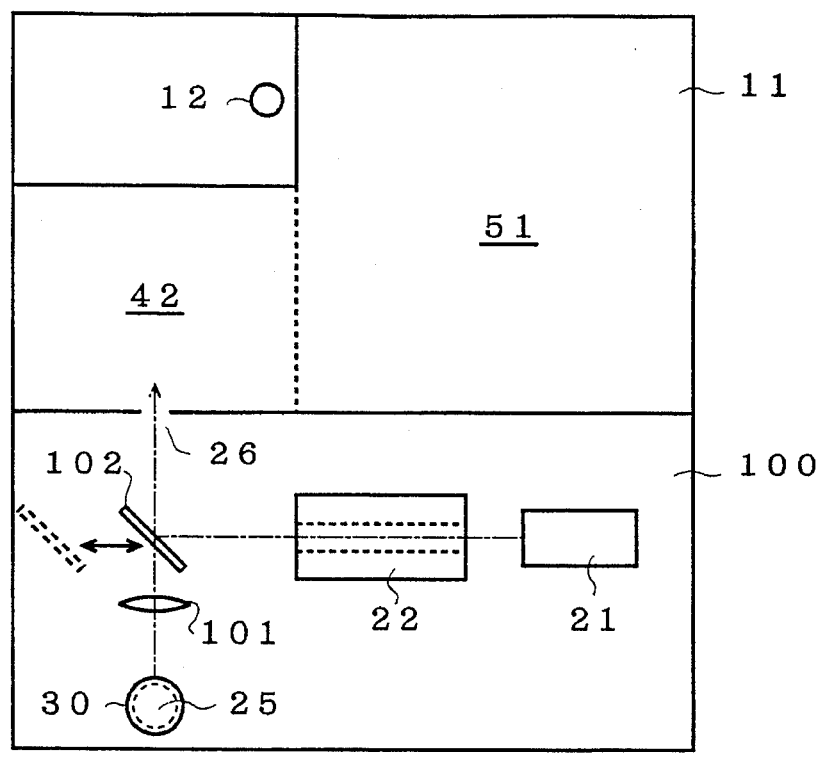
FIG. 10 is a block diagram illustrating a general structure of another apparatus applied to both ICP emission spectroscopy and atomic absorption spectrometry, as a second embodiment of the present invention.

Another embodiment of the present invention is illustrated in FIG. 10. A spectroscopic apparatus of the second embodiment has a sample table 100 fixed to the spectroscopic unit 11 shown in FIG. 4. The hollow cathode lamp 21 and the heating tube 22 for atomic absorption spectrometry and the plasma torch 30 for ICP emission spectroscopy are mounted on the sample table 100. A movable switching mirror 102 is also disposed on the sample table 100. In the ICP emission spectroscopic mode, a control unit moves the switching mirror 102 back to a position shown by the broken line to allow a light from the plasma flame 25 to pass through a converging lens 101 to the light inlet 26 of the spectroscopic unit 11. The echelle spectral element 52 is placed in the optical path in the spectroscopic unit 11. This allows a light produced by the preliminary spectral element 43 and the intermediate slit 50 to be further separated to a spectrum with high resolving power by the echelle spectral element 52 and the outlet slit 54 and to be detected by the detector 12.

In the atomic absorption spectrometric mode, the control unit moves the switching mirror 102 to a position shown by the solid line to allow a light passed through the heating tube 22 to enter the light inlet 26. In the spectroscopic unit 11, the echelle spectral element 52 is replaced by the plane light reflector 52b, which allows the spectrum produced by the preliminary spectral element 43 and the intermediate slit 50 to directly pass through the outlet slit 54 and to be detected by the detector 12. The spectroscopic unit 11 with the two detectors 12 and 14 as shown in FIG. 3 is also applicable to the spectroscopic apparatus of the second embodiment.

Figure 11:
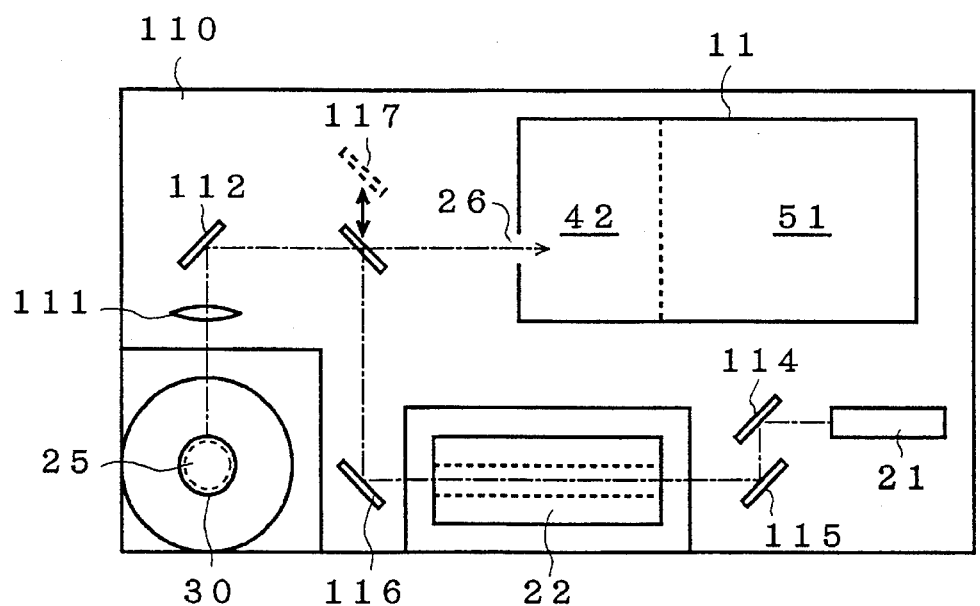
FIG. 11 is a block diagram illustrating a general structure of still another apparatus applied to both ICP emission spectroscopy and atomic absorption spectrometry, as a third embodiment of the present invention.

FIG. 11 shows still another embodiment of the present invention. In a spectroscopic apparatus of the third embodiment, while positions of the heating tube 22 and the plasma torch 30 are fixed on a sample table 110 like the embodiment shown in FIG. 10, a switching mirror 117 is moved to lead a desired light into the spectroscopic unit 11. The apparatus of the third embodiment has a converging lens 111 and light reflectors 112, 114, 115, and 116.

As described above, the spectroscopic apparatus of the present invention is applicable to both ICP emission spectroscopy and atomic absorption spectrometry by a simple switching operation. This significantly reduces the labor and time of the operator who requires both analyses. The spectroscopic unit of the present invention commonly used for both analyses reduces the size of the whole apparatus and the manufacturing cost. A common gas system and automatic switching of the gas flow path further make the operator free from troublesome and time-consuming operations and reduce the cost as well as the size of the apparatus.

There may be many modifications, alterations, and changes without departing from the scope or spirit of essential characteristics of the present invention. It is thus clearly understood that the above embodiments are only illustrative and not restrictive in any sense. The scope and spirit of the present invention are limited only by the terms of the appended claims.

What is claimed is:

1. A spectroscopic apparatus applied to both inductively coupled plasma (ICP) emission spectroscopy and atomic absorption spectrometry, said apparatus comprising:

(a) ICP emission means for exciting a sample to a plasma to produce a light including an emission spectrum of said sample;

(b) atomic absorption means for heating and atomizing a sample in a heating tube and allowing a light from a light source to pass through said atomized sample;

(c) first spectroscopic means for separating a light passed through a first light inlet to produce a first spectrum with a first spectral element;

(d) second spectroscopic means for separating a light passed through a second light inlet to produce a second spectrum with a second spectral element;

(e) light detection means for measuring an intensity of a light; and (f) control means operable in an ICP emission spectroscopic mode and in an atomic absorption spectrometric mode, where the control means leads the light from said ICP emission means to said first light inlet, introduces the light separated by said first spectroscopic means to said second light inlet, and introduces the light separated by said second spectroscopic means to said light detector means in the ICP emission spectroscopic mode, and leads the light emitted from the light source and passed through said atomic absorption means to said first light inlet and introduces the light separated by said first spectroscopic means to said light detector means in the atomic absorption spectrometric mode.

2. A spectroscopic apparatus according to claim 1, wherein said apparatus further comprises switching means for switching a gas supply from an inert gas source between said ICP emission means and said atomic absorption means, and said control means controls the switching means to connect the gas supply from said inert gas source to said ICP emission means in the ICP emission spectroscopic mode and controls the switching means to connect the gas supply from said inert gas source to said atomic absorption means in the atomic absorption spectrometric mode.

3. A spectroscopic apparatus according to claim 1, wherein said control means includes means for switching light led to said first light inlet by means of moving said ICP emission means and said atomic absorption means relative to said first spectroscopic means.

4. A spectroscopic apparatus according to claim 1, wherein said control means includes means for switching light led to said first light inlet by means of disposing a movable mirror in the optical path from either said ICP emission means or said atomic absorption means.

5. A spectroscopic apparatus according to claim 1, wherein said light detection means comprises only one light detector commonly used in the ICP emission spectroscopic mode and in the atomic absorption spectrometric mode; and said control means includes means for switching light entering to said light detector.

6. A spectroscopic apparatus according to claim 1, wherein said light detection means comprises separate two light detectors used in the ICP emission spectroscopic mode and in the atomic absorption spectrometric mode independently.

* * * * *